(12) United States Patent
Young (10) Patent No.: US 12,029,888 B2
(45) Date of Patent: Jul. 9, 2024

(54) SAFETY WARNING SYSTEM (71) Applicant: THE QUEEN ELIZABETH HOSPITAL KING'S LYNN NHS FOUNDATION TRUST, King's Lynn (GB)

(72) Inventor: Peter Jeffrey Young, King's Lynn (GB)

(73) Assignee: THE QUEEN ELIZABETH HOSPITAL KING'S LYNN NHS FOUNDATION TRUST, Norfolk (GB)

( * ) Notice: Subject to any disclaimer, the term of this patent is extended or adjusted under 35 U.S.C. 154(b) by 1022 days.

(21) Appl. No.: 15/573,397

(22) PCT Filed: May 11, 2016

(86) PCT No.: PCT/GB2016/051351
§ 371 (c)(1),
(2) Date: Apr. 16, 2018

(87) PCT Pub. No.: WO2016/181141
PCT Pub. Date: Nov. 17, 2016

(65) Prior Publication Data
US 2018/0085538 A1 Mar. 29, 2018

(30) Foreign Application Priority Data

May 11, 2015 (GB) .................................. 1508017.9
Jun. 16, 2015 (GB) .................................. 1510599.2
Jan. 15, 2016 (GB) .................................. 1600802.1

(51) Int. Cl.
*A61M 5/50* (2006.01)
*A61M 5/14* (2006.01)
(Continued)

(52) U.S. Cl.
CPC ............ *A61M 5/5086* (2013.01); *A61M 5/14* (2013.01); *A61M 5/168* (2013.01);
(Continued)

(58) Field of Classification Search
CPC ........ A61B 5/1486; A61M 2005/1403; A61M 2205/0227; A61M 2205/18;
(Continued)

(56) References Cited

U.S. PATENT DOCUMENTS

2006/0188407 A1* 8/2006 Gable ................ A61B 5/15003
604/19
2008/0014601 A1* 1/2008 Goldberger ............ A61B 5/153
435/14

(Continued)

FOREIGN PATENT DOCUMENTS

EP 282806 9/1988
WO WO 2009/114115 9/2009

OTHER PUBLICATIONS

International Search Report and Written Opinion issued in International Application No. PCT/GB2016/051351, dated Nov. 14, 2016.

*Primary Examiner* — Kai H Weng
(74) *Attorney, Agent, or Firm* — Norton Rose Fulbright US LLP (57) ABSTRACT

A safety warning system for detecting glucose in an arterial monitoring or flush system is disclosed. An example of the system comprises a receptacle configured to receive fluid from a line for connecting to a patient, and an indicator arranged to contact the fluid and configured to provide an indication of whether the fluid comprises glucose. The receptacle comprises a gas release path to enable the fluid to displace gas to contact the indicator.

18 Claims, 7 Drawing Sheets

(51) Int. Cl.
*A61M 5/168* (2006.01)
*A61M 39/22* (2006.01)
*A61M 39/24* (2006.01)
*A61B 5/1486* (2006.01)

(52) U.S. Cl.
CPC ...... *A61M 5/16831* (2013.01); *A61M 39/223* (2013.01); *A61M 39/24* (2013.01); *A61B 5/1486* (2013.01); *A61M 2005/1403* (2013.01); *A61M 2205/0227* (2013.01); *A61M 2205/18* (2013.01); *A61M 2205/33* (2013.01); *A61M 2205/581* (2013.01); *A61M 2205/583* (2013.01); *A61M 2205/584* (2013.01); *A61M 2205/6081* (2013.01); *A61M 2230/201* (2013.01); *A61M 2230/30* (2013.01)

(58) Field of Classification Search
CPC ........ A61M 2205/33; A61M 2205/581; A61M 2205/583; A61M 2205/584; A61M 2205/6081; A61M 2230/201; A61M 2230/30; A61M 39/223; A61M 39/24; A61M 5/14; A61M 5/168; A61M 5/16831; A61M 5/5086
See application file for complete search history.

(56) References Cited

U.S. PATENT DOCUMENTS

| | | |
|---|---|---|
| 2008/0045825 A1* | 2/2008 | Melker .................. A61B 5/083 600/529 |
| 2008/0097288 A1 | 4/2008 | Levin et al. |
| 2008/0208024 A1* | 8/2008 | Hagino .............. A61B 5/14514 600/347 |
| 2012/0065482 A1 | 3/2012 | Robinson et al. |
| 2013/0289540 A1* | 10/2013 | Zeltser .................... A61M 1/28 604/891.1 |
| 2014/0275908 A1 | 9/2014 | Zamarripa et al. |
| 2015/0112248 A1* | 4/2015 | Helliwell ............. A61B 5/1473 604/28 |

* cited by examiner

SAFETY WARNING SYSTEM

CROSS-REFERENCE TO RELATED APPLICATIONS

This application is a national phase application under 35 U.S.C. § 371 of International Application No. PCT/GB2016/051351, filed May 11, 2016, which claims priority to United Kingdom Application No. 1508017.9, filed May 11, 2015, United Kingdom Application No. 1510599.2, filed Jun. 16, 2015, and United Kingdom Application No. 1600802.1, filed Jan. 15, 2016. The entire contents of which applications are incorporated herein by reference.

FIELD OF THE INVENTION

The present disclosure relates to a safety warning system, for example a safety warning system for detecting glucose in medical lines coupled to vasculature, such as lines of arterial or venous monitoring or flush systems, and venous agent delivery systems, for example drug delivery systems.

BACKGROUND

Arterial lines are routinely used in critical care areas for sampling arterial blood to measure blood pressure, gases, glucose and electrolytes. Venous lines may also be used for such monitoring, and may also be used for drug delivery. Infusions, such as a saline solution may be used to keep the line open. Patients may be harmed if the wrong infusion is given to keep the line open or when poor sampling leads to delayed or inappropriate treatment.

SUMMARY OF THE INVENTION

Aspects of the invention are as set out in the independent claims and optional features are set out in the dependent claims. Aspects of the invention may be provided in conjunction with each other and features of one aspect may be applied to other aspects.

DRAWINGS

Embodiments of the disclosure will now be described, by way of example only, with reference to the accompanying drawings, in which.

SPECIFIC DESCRIPTION

Embodiments of the disclosure relate to a safety warning system that warns clinicians if a glucose containing solution is being used with an arterial or venous monitoring or flush system.

Figure 1:
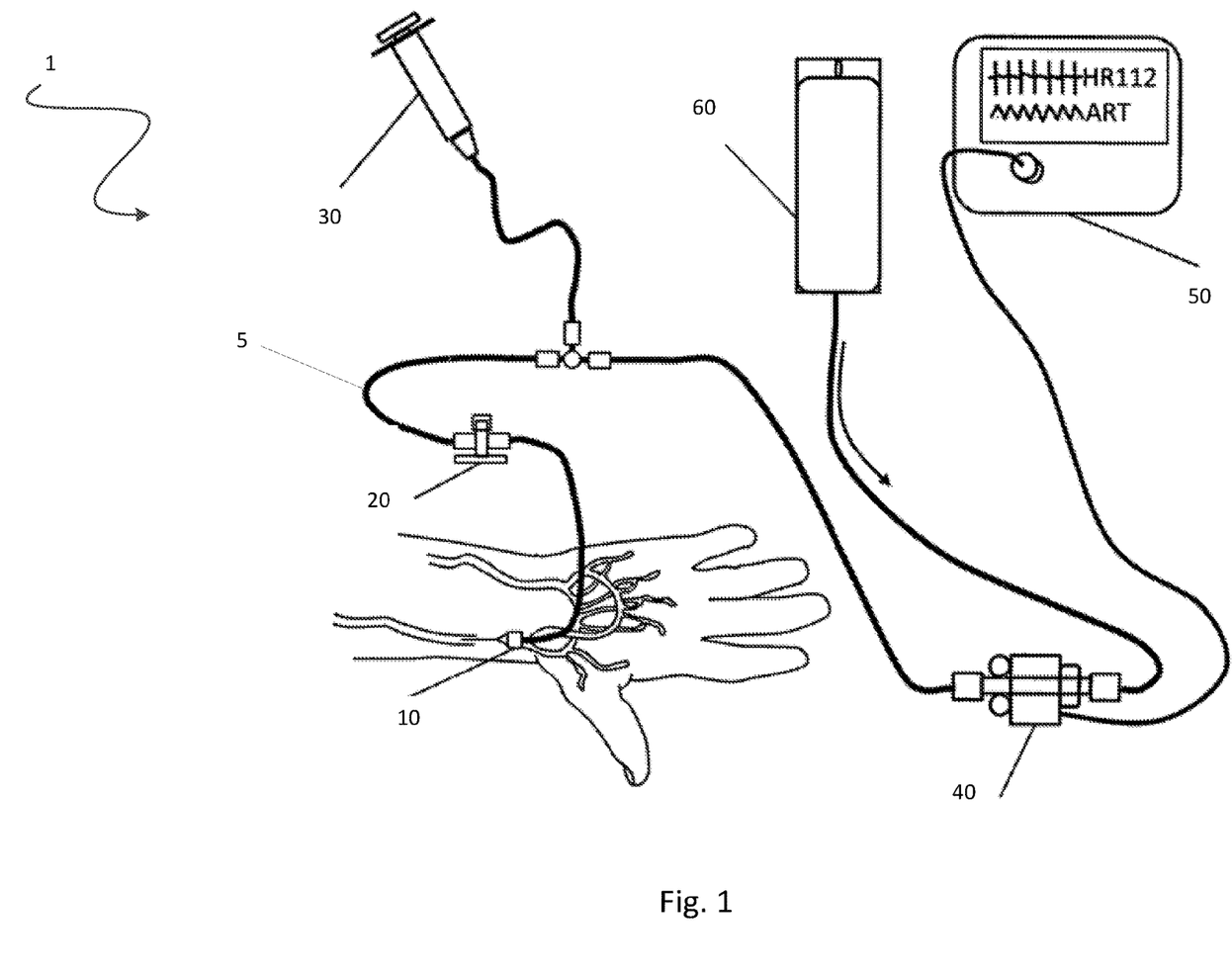
FIG. 1 shows a schematic view of an arterial monitoring system.

FIG. 1 shows an arterial pressure monitoring system 1 suitable for use with examples of the disclosure. Although an arterial pressure monitoring system 1 is shown and described, it will be appreciated that examples of the disclosure may be used with any system that is coupled to the vasculature, such as a venous monitoring system or an arterial or venous flush system.

The arterial pressure monitoring system 1 typically comprises an arterial line 5, which has low compliance tubing for accuracy in monitoring. At one end of the line 5, the system 1 comprises an indwelling cannula 10 for insertion into a patient from which arterial pressures are continuously measured. A port 20 allowing clinicians to draw blood samples as needed may be located upstream of the cannula 10. A syringe 30 may also be coupled to the line 5 for drawing back blood or solution to clear the line 5 as necessary.

A three-way port 40, such as a Luer® port, is coupled to the line 5 upstream of the port 20 and syringe 30, and typically comprises a transducer. The three-way port 40 and transducer allows clinicians to regulate flow in the line 5 and transforms the mechanical energy of the arterial pressure through the line 5 into an electrical signal for display as a waveform by a haemodynamic monitor 50. A bag of pressurised medical fluid 60, typically at a pressure of at least 200 mmHg, is coupled to the three-way port 40, typically via a spike, and provides a steady flush of an infusion fluid, for example of about 3 to 4 mL/hr through the line 5. Typically a saline flush such as a solution or infusion of sodium chloride 0.9% is used as the medical fluid for arterial lines.

Prior to use of the arterial pressure monitoring system 1 the line 5 has to be prepared. The line 5 is cleared of gas as this may be dangerous to patients and may affect the pressure reading recorded by the monitor 50. To clear the line 5, a clinician may squeeze the three-way port 40 to open it up and allow a higher flow rate of fluid to flow through it. For example, by squeezing the three-way port 40, the flow rate may increase up to 40 mL/hr or greater. A medical fluid is used to clear the gas. Once the gas is cleared, the medical fluid is maintained at pressure and a constant flow rate, for example at about 3 to 4 mL/hr. This is in part to counter the natural pressure of an artery into which the cannula is inserted, in part to keep the line 5 open and prevent clotting, and in part to ensure effective monitoring of the patient.

As noted above, glucose containing solutions should not be used in arterial monitoring or flush systems because this can cause contamination of samples with glucose and incorrect blood glucose readings. In a clinical environment a bag of glucose solution and a bag of saline solution may look very similar. Embodiments of the disclosure may address these problems by providing a safety warning system that detects whether glucose has been used and provides an indication to the user, such as a clinician, typically a visual indication.

Figure 2:
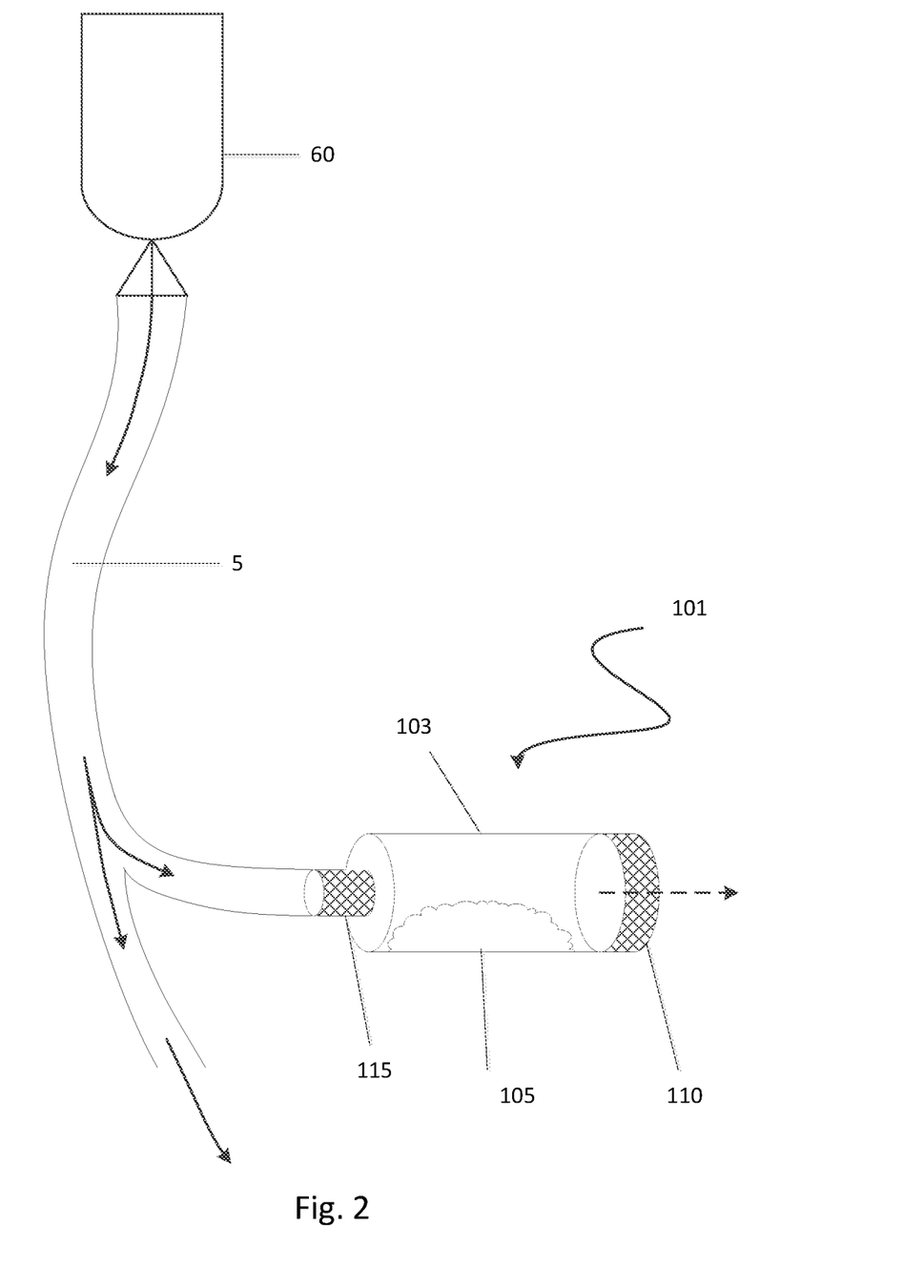
FIG. 2 shows a schematic view of an example safety warning system.
Figure 3:
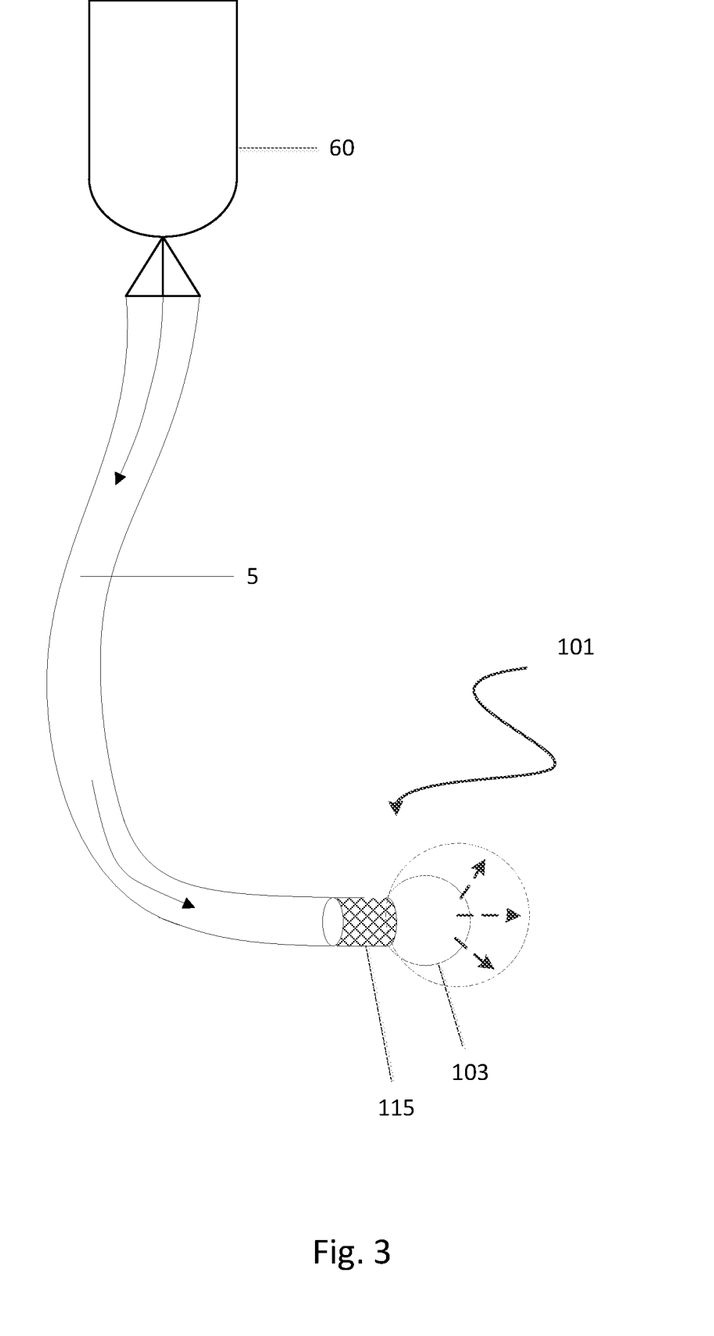
FIG. 3 shows a schematic view of an example safety warning system.
Figure 4:
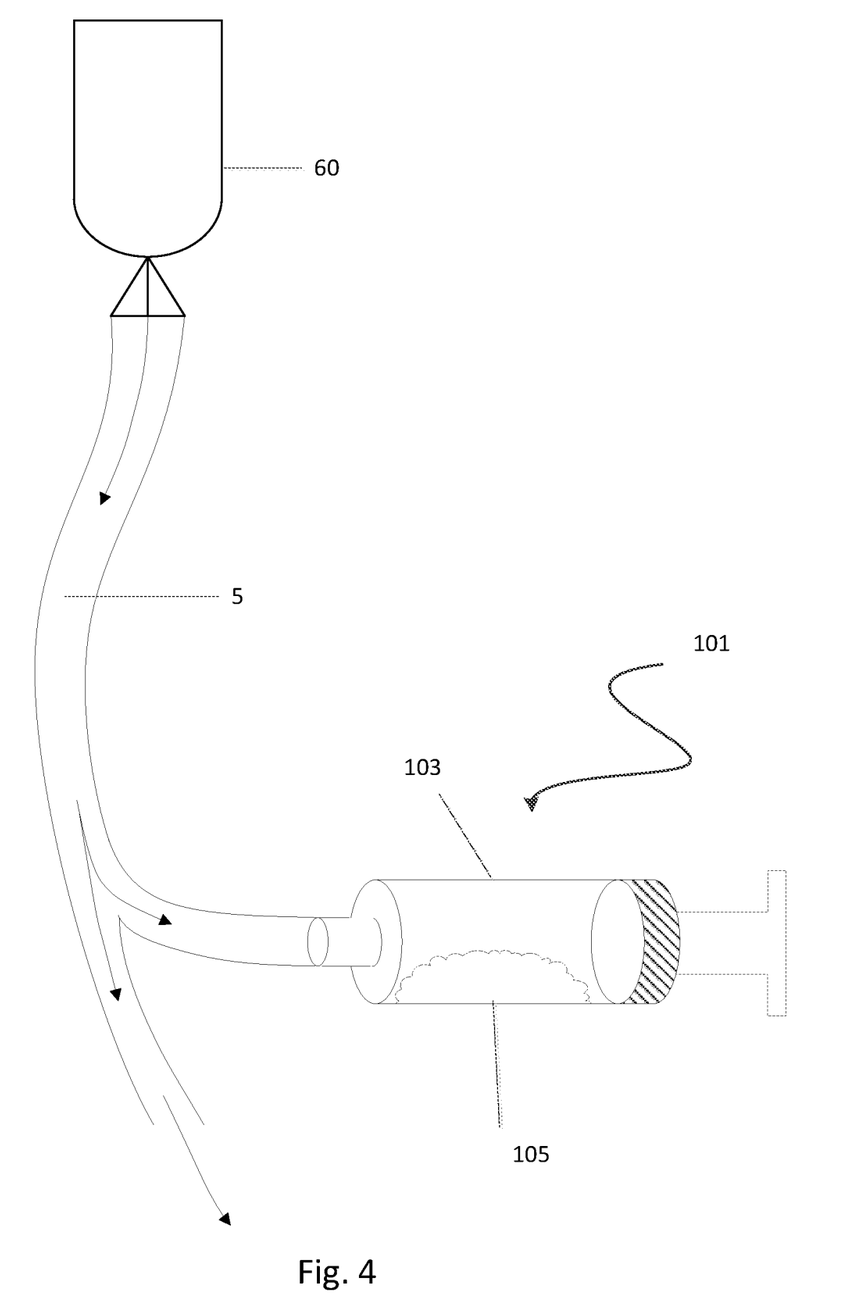
FIG. 4 shows a schematic view of an example safety warning system.
Figure 5:
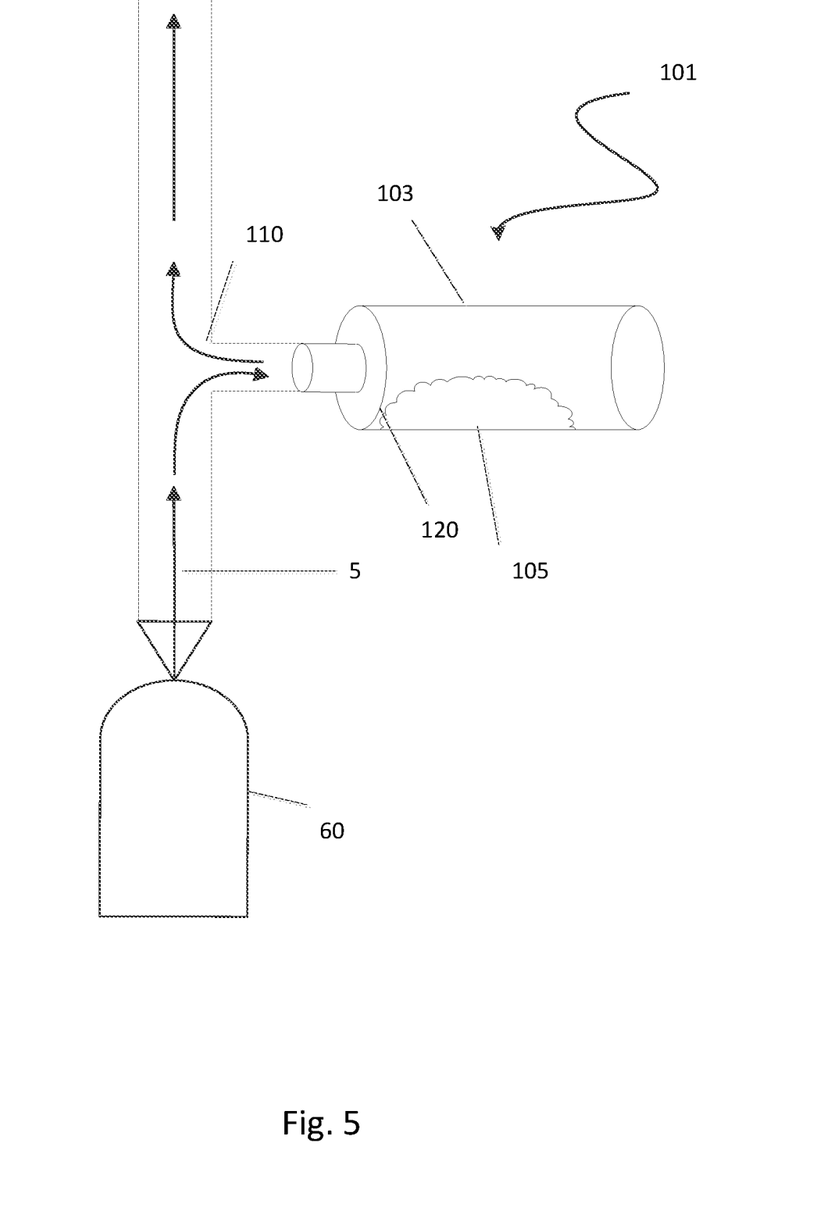
FIG. 5 shows a schematic view of an example safety warning system.
Figure 6:
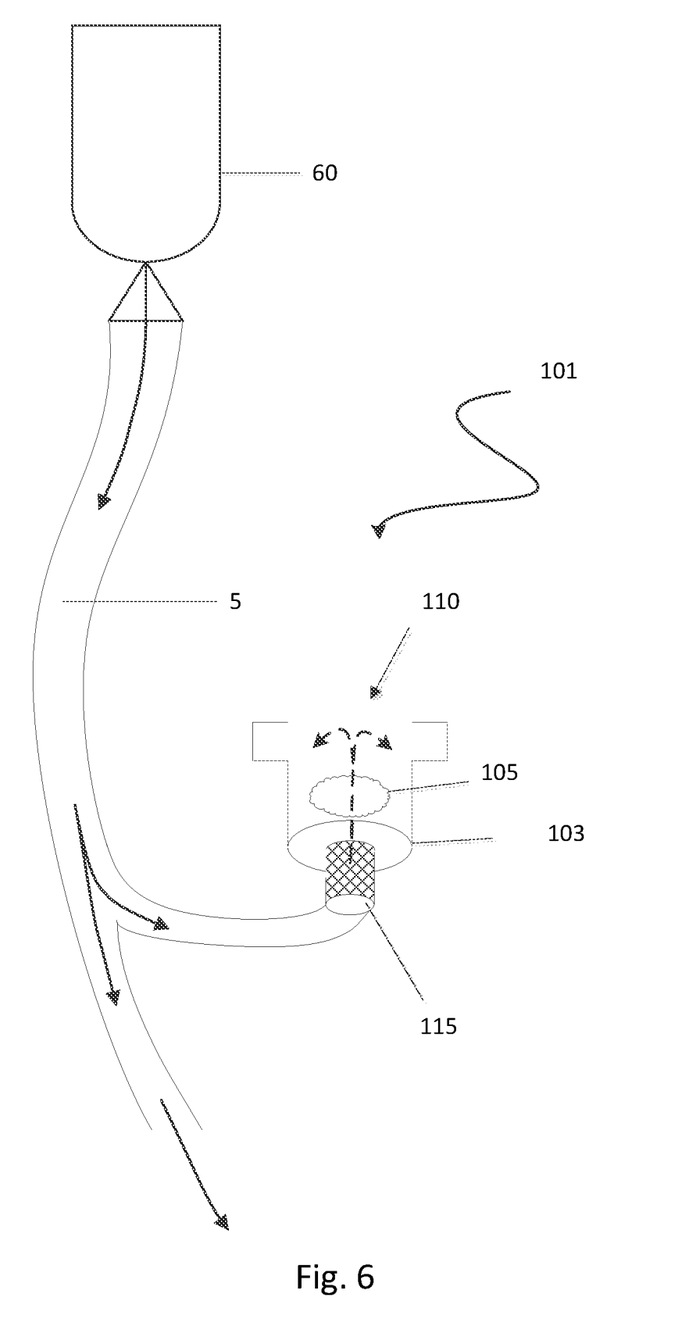
FIG. 6 shows a schematic view of an example safety warning system.

Embodiments of the claims may do this by providing, as shown in FIGS. 2 to 6, a safety warning system 101 comprises a receptacle 103 for the clinician to flush the fluid, for example the initial gas in the line 5 and a first quantity of the solution, into. The system 101 also comprises an indicator 105 arranged to contact the fluid that provides an indication of whether the fluid comprises glucose. The receptacle 103 may be expandable to receive the fluid, or as shown in FIGS. 2, 5 and 6, may comprise a gas release path 110 to enable the fluid to displace gas to contact the indicator 105.

Expandable receptacles may include receptacles 103 that are themselves configured to expand, such as a balloon (as described in FIG. 3), or receptacles 103 that are configured to expand so that a fluid receiving cavity inside the receptacle increases in volume, such as a syringe and plunger (as described in FIG. 4).

It will be appreciated from the discussion above that the embodiments shown in the Figures are merely exemplary, and include features which may be generalised, removed or replaced as described herein and as set out in the claims.

In more detail, FIG. 2 shows a bag of medical fluid 60 coupled to a medical or surgical line 5. In this example the medical fluid is a liquid saline solution. The line 5 comprises a branch downstream of the bag of medical fluid 60 and on one of the branches a receptacle 103 is coupled to the line 5. The other branch provides an outlet. In other examples, however, the line 5 does not have a branch and the receptacle 103 is coupled to the outlet of the line 5 (for example, as shown in FIG. 3 and as described below). In such examples, the safety warning system 101 may be provided as a cap to the line 5, and may need to be removed and optionally discarded before the line 5 is able to be used. For example, the cap may inhibit the line 5 from being connected to the patient until it is removed. For example, the safety warning system 101 is configured to be disposable. Providing the safety warning system 101 so that it couples to the outlet of the line 5 may also help to keep the line 5 sterile prior to use, and because it has to be removed before the line is coupled to a patient, it is more prominent to a clinician if the indicator 105 provides an indication of whether the fluid comprises glucose. In some examples, the safety warning system 101 is provided pre-coupled to the line 5 so that a user such as a clinician does not forget to couple it to the line 5 prior to use, who has to take an active step of removing the safety warning system 101 prior to connecting the line 5 to a patient.

Other components such as those described above in relation to FIG. 1, such as the three-way port 40, may also be coupled to the line upstream of the safety warning system 101 and downstream of the bag of medical fluid 60.

The safety warning system 101 shown in FIG. 2 comprises a receptacle 103 comprising a syringe with a gas release path 110, comprising a gas release valve, instead of a plunger. The receptacle 103 has a cavity having a volume of at least 5 mL, although it may have a volume of at least 20 or at least 30 mL. Inside the receptacle 103 is an indicator 105 which in this example is a chemical indicator, such as glucose oxidase and/or peroxidase. In the example shown, the indicator 105 is configured to change colour in contact with a glucose-containing solution. For example, the indicator 105 may comprise a dye, such as toluene blue, that is released upon a chemical reaction between the indicator and a glucose-containing solution. Other nanoparticle, nanorod and nano-chain based indicators may be used. Indicators based on the Fenton reaction and indicators based on a hydrogen bubble porous gold technique may also be used.

The indicator 105 is adapted to contact the fluid from the line 5, and in the example shown in FIG. 2, is arranged to contact fluid in the receptacle 103. The safety warning system 101 comprises a one-way valve 115 to one side of the indicator 103 in the receptacle 103, and a gas release valve that acts as a gas release path 110 to the other side of the indicator 105 in the receptacle 103 so that fluid from the line 5 comes into contact with the indicator 105. In the example shown in FIG. 2, the one-way valve 115 is at one end of the receptacle 103, and the gas release valve is at the other end of the receptacle 103, although the gas release valve may be located elsewhere on the receptacle 103. In other examples, however, the safety warning system 101 does not comprise a one-way valve 115.

The line 5 is adapted for connecting to a patient. The receptacle 103 is configured to receive fluid from the line 101 so that fluid received from the line 5 can be displaced into the cavity. The one-way valve 115 is configured to allow fluid to flow from the line 5 into the receptacle 103. The gas release valve provides a gas release path 110 and is operable to enable fluid to displace gas to contact the indicator 105. For example, the gas release valve is operable to allow medical fluid, such as liquid saline, to flow down the line 5 and through the one-way valve 115 into the receptacle 103, thereby displacing gas in both the line 5 and inside the receptacle 103.

The gas release valve in this example is configured to block in contact with liquid. The gas release valve may comprise a porous membrane, such as an air-permeable membrane, for example a microporous hydrophobic membrane (MHM). Depending on the membrane, the pore size may range from 0.01 to more than 10 μm. The membrane may be configured to react to the presence of liquid. For example, the membrane may swell in contact with liquid, or may react with the liquid, so that the membrane is no longer porous or air-permeable. For example, the membrane may comprise a chemical that reacts with the liquid. The membrane may comprise polymers such as polytetrafluoroethylene (PTFE), polypropylene, polyvinylidene difluoride (PVDF) and acrylic copolymers. The gas release valve is configured to allow gas to flow therethrough, but prevents or inhibits the flow of liquid therethrough.

In this way, the receptacle retains liquid flushed through the line 5. This may allow a clinician to prep and flush the line by a patient's bedside, without requiring a sink or drain. It also means that solution flushed through the line 5, and the indicator 105, is not lost.

In use, a clinician wishing to set up, for example an arterial monitoring system, attaches the receptacle 103 to an outlet of the line 5, and a bag of medical fluid 60 to an input of the line 5. An optional spike may be used to pierce the bag of medical fluid 60 and couple the line 5 to the bag of medical fluid 60. The spike may be irreversible to inhibit removal of the bag of medical fluid 60, for example the spike may be barbed, for example the spike may comprise a unidirectional barb. The clinician allows the medical fluid to flow through the line 5 so that any initial gas in the line 5 is displaced by the medical fluid. The clinician may apply pressure to the fluid to allow it flow through the line 5 and into the receptacle 103, for example the bag of medical fluid 60 may be pressurised or may be squeezed by a device to provide pressure to the fluid.

The fluid in the line 5, comprising any initial gas in the line 5 and the medical fluid, flows via bulk flow through the one-way valve 115 and into the cavity of the receptacle 103. To ensure the fluid flows into the safety warning system 101, the user may wish to block off the other branch in the line 5 (if present), for example using a tap or valve such as a three-way port such as a Luer® port. The gas release valve allows the gas to flow out of the receptacle 103, but because it blocks in contact with liquid, it blocks to prevent the medical fluid (which in this example is liquid saline), and the chemical indicator 115, from escaping from the receptacle 103.

If the solution flowing through the line 5 comprises glucose, the indicator 105 provides a visual indication to the clinician, and in this case will change colour (for example to a dark blue colour) to indicate to the clinician that a glucose-containing solution has been used. Once the line 5 has been flushed, the safety warning system 101 may in some examples be removed before use such as in an arterial monitoring system, or in other examples may remain coupled to the line 5.

In the example described above the gas release valve blocks in contact with liquid. In other examples, the safety warning system 101 may comprise a user-operated tap or valve to allow fluid to escape from the receptacle 103 and/or the line 5. For example, the receptacle 103 may comprise a valve or tap that has a first configuration that is open and a second configuration that is closed, and that may be biased to rest in the second configuration. For example, the tap or valve may open when operated by a clinician but closes automatically again at rest.

Although the indicator 105 shown in FIG. 2 is arranged to contact fluid inside the receptacle 105, in other examples the indicator 105 may be arranged to contact fluid in the one-way valve 115 or in the gas release path 110. The indicator 105 may be arranged to be in a wall of the receptacle 103, or in a wall of the one-way valve 115 or gas release path 110. For example, the indicator 105 may be arranged to be on the inside wall of the one-way valve 115, so that it contacts fluid that has just passed through the one-way valve 115.

FIG. 3 shows another example safety warning system 101 that comprises an expandable receptacle 103 to receive fluid from a line 5. As described above in relation to FIG. 2, FIG. 3 shows a bag of medical fluid 60 coupled to a medical or surgical line 5. The medical fluid 60 in this example is again a liquid saline solution. A receptacle 101 comprising a cavity is coupled to the outlet of the the line 5 downstream of the bag of medical fluid 60. In other examples, however, the line 5 has a branch and the receptacle 101 is coupled to the line 5 via the branch. Other components such as those described above in relation to FIG. 1, such as the three-way port 40, such as a three-way Luer® valve, may also be coupled to the line upstream of the safety warning system 101 and downstream of the bag of medical fluid 60.

The safety warning system 101 shown in FIG. 3 comprises a receptacle 103 broadly in the shape of a balloon. The safety warning system 101 comprises a one-way valve 115 interposed between the receptacle 103 and the line 5. As with the example described above in relation to FIG. 2, the receptacle 103 comprises an indicator 105 which in this example is a chemical indicator which changes colour in contact with a glucose-containing solution. The indicator 105 is adapted to contact the fluid from the line 5, and in the example shown in FIG. 3, is arranged to contact fluid in the receptacle 103.

The line 5 is adapted for connecting to a patient. The receptacle 103 is configured to receive fluid from the line 101. The one-way valve 115 is configured to allow fluid to flow from the line 5 into the receptacle 103. The receptacle 103 is expandable and configured to expand to receive fluid from the line 5. The receptacle 103 may have a volume of at least 5 mL, or be expandable to have a volume of at least 5 mL, or at least 20 mL or at least 30 mL. In the example shown in FIG. 3, the receptacle 103 is configured to expand to receive a volume of fluid greater than or equal to the internal volume of the line 5.

In the example shown in FIG. 3, the receptacle 103 is closed so that it retains fluid received from the line 5. This may allow a clinician to prep and flush the line by a patient's bedside, without requiring a sink or drain. It also means that solution flushed through the line 5, and the indicator 105, is not lost.

In use, as with the example described above in relation to FIG. 2, a clinician wishing to set up, for example an arterial monitoring system, attaches the receptacle 103 to an outlet of the line 5, and a bag of medical fluid 60 to an input of the line 5. The clinician allows the medical fluid to flow through the line 5 so that any initial gas in the line 5 is displaced by the medical fluid. The fluid in the line 5, comprising any initial gas and the medical fluid, flows via bulk flow through the one-way valve 115 and into the cavity in the receptacle 103. Because the receptacle 103 is closed, it expands to receive the fluid comprising the gas and the medical fluid. Because the receptacle 103 is closed, it also prevents medical fluid, and in this case the chemical indicator, from escaping from the receptacle 103.

If the solution flowing through the line 5 comprises glucose, the indicator 105 provides a visual indication to the clinician, and in this case will change colour (for example to a dark blue colour) to indicate to the clinician that a glucose-containing solution has been used. Once the line 5 has been flushed, the safety warning system 101 may in some examples be removed before use such as in an arterial monitoring system, or in other examples may remain coupled to the line 5.

FIG. 4 shows another example safety warning system 101 that, as with the example described above in relation to FIG. 3, comprises an expandable receptacle 103 to receive fluid from a line 5. As described above in relation to FIGS. 2 and 3, FIG. 4 shows a bag of medical fluid 60 coupled to a medical or surgical line 5. The medical fluid in this example is again a liquid saline solution. The line 5 comprises a branch downstream of the bag of medical fluid 60 and on one of the branches a receptacle 101 comprising a cavity is coupled to the line 5. In other examples, however, the line 5 does not have a branch and the receptacle 101 is coupled to an outlet of the line 5. Other components such as those described above in relation to FIG. 1, such as the three-way port 40, may also be coupled to the line upstream of the safety warning system 101 and downstream of the bag of medical fluid 60.

The safety warning system 101 shown in FIG. 4 comprises a receptacle 103 that is a syringe, and may be the syringe 30 shown in FIG. 1. The safety warning system 101 may also comprise an optional one-way valve 115 (not shown) interposed between the receptacle 103 and the line 5. As with the example described above in relation to FIGS. 2 and 3, the receptacle 103 comprises an indicator 105 which in this example is a chemical indicator which changes colour in contact with a glucose-containing solution. The indicator 105 is adapted to contact the fluid from the line 5, and in the example shown in FIG. 4, is arranged to contact fluid in the receptacle 103.

As with the example described above in relation to FIG. 3, the line 5 is adapted for connecting to a patient. The receptacle 103 is configured to receive fluid from the line 101. The receptacle 103 is operable by a user, such as a clinician, to draw fluid from the line 5. The receptacle 103 is expandable and when operated by the user expands to receive fluid from the line 5. The receptacle 103 shown in FIG. 4 expands so that a fluid receiving cavity inside the receptacle 103 increases in volume. In the example shown, the receptacle 103 (in this case a syringe) expands by forcing a plunger of the syringe outwards, to increase the internal volume of the syringe. In the example shown in FIG. 4, the receptacle 103 is also configured to expand to receive a volume of fluid greater than or equal to the internal volume of the line 5.

In the example shown in FIG. 4, the receptacle 103 is closed so that it retains fluid received from the line 5. This may allow a clinician to prep and flush the line by a patient's bedside, without requiring a sink or drain. It also means that solution flushed through the line 5, and the indicator 105, is not lost.

In use, as with the example described above in relation to FIGS. 2 and 3, a clinician wishing to set up, for example an arterial monitoring system, attaches the receptacle 103 to an outlet of the line 5, and a bag of medical fluid 60 to an input of the line 5. The clinician allows the medical fluid to flow through the line 5 so that any initial gas in the line 5 is displaced by the medical fluid. The clinician operates the receptacle 103 to draw fluid from the line 5, comprising any initial gas and the medical fluid, into the cavity of the receptacle 103 via bulk flow. As the receptacle 103 is operated by the clinician, its internal volume expands to receive the fluid comprising the gas and the medical fluid. Because the receptacle 103 is closed, it also prevents medical fluid, and in this case the chemical indicator, from escaping from the receptacle 103.

As with the examples described above, if the solution flowing through the line 5 comprises glucose, the indicator 105 provides a visual indication to the clinician, and in this case will change colour (for example to a dark blue colour) to indicate to the clinician that a glucose-containing solution has been used. Once the line 5 has been flushed, the safety warning system 101 may in some examples be removed before use such as in an arterial monitoring system, or in other examples may remain coupled to the line 5.

FIG. 5 shows another example safety warning system 101 that comprises a receptacle 103 broadly in the shape of a cylinder with a gas release path 110. The safety warning system 101 comprises a port 120 at one end of the receptacle 103, and is sealed at the other end. The receptacle 103 comprises a cavity and is coupled to a branch in a medical or surgical line 5 via the port 120.

Inside the receptacle 103 is an indicator 105 which in this example is a chemical indicator which changes colour in contact with a glucose-containing solution. The indicator 105 is adapted to contact the fluid from the line 5, and in the example shown in FIG. 2, is arranged to contact fluid in the receptacle 103.

The medical or surgical line 5 is coupled to a bag of medical fluid 60, which in this example is again a liquid saline solution. The branch in the line 5 to which the safety warning system is coupled provides a gas release path 110 for gas to escape the receptacle 103.

The line 5 is adapted for connecting to a patient. The receptacle 103 is configured to receive fluid from the line 101. The port 120 is configured to allow fluid to flow from the line 5 into the receptacle 103, and to allow gas to escape from the receptacle 103 via the gas release path 110. The gas release path 110 enables fluid to displace gas to contact the indicator 105 in the receptacle 103. For example, the gas release path 110 allows medical fluid, such as liquid saline, to flow along the line 5 and through the port 120 into the receptacle 103, thereby displacing gas in both the line 5 and inside the receptacle 103.

In use, a clinician wishing to set up, for example an arterial monitoring system, attaches the receptacle 103 to an outlet of the line 5, and a bag of medical fluid 60 to an input of the line 5. The clinician allows the medical fluid to flow through the line 5 so that any initial gas in the line 5 is displaced by the medical fluid. The fluid in the line 5, comprising the initial gas and the liquid, flows via bulk flow through the port 120 and into the cavity of the receptacle 103. The port 120 and gas release path 110 allows any gas in the line 5 and in the receptacle 103 to escape thereby being displaced by liquid.

As with the examples described above, if the solution flowing through the line 5 comprises glucose, the indicator 105 provides a visual indication to the clinician, and in this case will change colour (for example to a dark blue colour) to indicate to the clinician that a glucose-containing solution has been used. Once the line 5 has been flushed, the safety warning system 101 may in some examples be removed before use such as in an arterial monitoring system, or in other examples may remain coupled to the line 5.

Although the indicator 105 shown in FIG. 5 is arranged to contact fluid inside the receptacle 105, in other examples the indicator 105 may be arranged to contact fluid in the one-way valve 115 or in the gas release path 110. The indicator 105 may be arranged to be in a wall of the receptacle 103, or in a wall of the one-way valve 115 or gas release path 110. For example, the indicator 105 may be arranged to be on the inside wall of the one-way valve 115, so that it contacts fluid that has just passed through the one-way valve 115.

FIG. 6 shows another example safety warning system 101 that comprises a receptacle 103 broadly in the shape of a cup with a gas release path 110. The safety warning system 101 comprises a one-way valve 115 at one end of the receptacle 103, and is open at the other end. The receptacle 103 comprises a cavity and is coupled to a branch in a medical or surgical line 5 via the one-way valve 115.

Inside the receptacle 103 is an indicator 105 which in this example is a chemical indicator which changes colour in contact with a glucose-containing solution. The indicator 105 is adapted to contact the fluid from the line 5, and in the example shown in FIG. 6, is arranged to contact fluid in the receptacle 103.

The medical or surgical line 5 is coupled to a bag of medical fluid 60, which in this example is again a liquid saline solution. The open end of the receptacle 103 provides a gas release path 110 for gas to escape the receptacle 103.

The line 5 is adapted for connecting to a patient. The receptacle 103 is configured to receive fluid from the line 101. The one-way valve 115 is configured to allow fluid to flow from the line 5 into the receptacle 103. The gas release path 110 enables fluid to displace gas in the receptacle 103 to contact the indicator 105 in the receptacle 103. For example, the gas release path 110 allows medical fluid, such as liquid saline, to flow along the line 5 and through the one-way valve 115 into the receptacle 103, thereby displacing gas in both the line 5 and inside the receptacle 103.

In use, a clinician wishing to set up, for example an arterial monitoring system, attaches the receptacle 103 to an outlet of the line 5, and a bag of medical fluid 60 to an input of the line 5. The clinician allows the medical fluid to flow through the line 5 so that any initial gas in the line 5 is displaced by the medical fluid. The fluid in the line 5, comprising the initial gas and the liquid, flows via bulk flow through the one-way valve 115 and into the cavity of the receptacle 103. The gas release path 110 allows gas in the line 5 and in the receptacle 103 to escape thereby being displaced by liquid which fills the receptacle 103.

In the example shown in FIG. 6, the receptacle 103 is generally held upright to prevent the loss of liquid, although in other examples the receptacle may comprises a valve to enable fluid such as gas to escape the receptacle 103, such as a gas release valve. For example, the receptacle 103 may comprise a valve or tap, such as a Luer® fitting, that has a first configuration that is open and a second configuration that is closed, and that may be biased to rest in the second configuration. For example, the tap or valve may open when operated by a user but closes automatically again at rest.

As with the examples described above, if the solution flowing through the line 5 comprises glucose, the indicator 105 provides a visual indication to the clinician, and in this case will change colour (for example to a dark blue colour) to indicate to the clinician that a glucose-containing solution has been used. Once the line 5 has been flushed, the safety warning system 101 may in some examples be removed before use such as in an arterial or venous monitoring system, or in other examples may remain coupled to the line 5.

Although the indicator 105 shown in FIG. 6 is arranged to contact fluid inside the receptacle 105, in other examples the indicator 105 may be arranged to contact fluid in the one-way valve 115 or in the gas release path 110. The indicator 105 may be arranged to be in a wall of the receptacle 103, or in a wall of the one-way valve 115 or gas release path 110. For example, the indicator 105 may be arranged to be on the inside wall of the one-way valve 115, so that it contacts fluid that has just passed through the one-way valve 115.

The safety warning system 101 described above may be provided in a sealed sterile pack, for example as part of a giving set, for example for use as an arterial or venous monitoring or flush system.

Providing the safety warning system 101 as part of giving set may mean that a user such as a clinician is presented with a single, user-openable, sterile pack that contains many, if not all, of the components necessary for an arterial or venous monitoring or flush system to be prepared for use. The single sterile pack may hold the components in a common enclosure, which can be opened to provide access to the components by a single mechanical action, such as tearing or puncturing a wall of that enclosure. The user knows that all of the components in the pack are sterile and safe ready for use, and that they are compatible and will fit together. Providing the giving set may also mean that incorrect or incompatible components are not used incorrectly or by mistake.

The safety warning system 101 may be supplied already coupled to the line 5, so that a clinician does not forget to attach it to the line 5, for example to the outlet of the line 5 so that the user has to take an active step of removing the safety warning system 101 before the line 5 can be used. The giving set may be provided as a sealed sterile pack. The giving set may comprise many of the components described above in relation to FIG. 1. For example, the giving set may comprise a medical or surgical line 5, a spike for insertion into a bag of medical fluid 60 (such as the spike described above), configured to couple the bag 60 to the medical or surgical line 5, and a safety warning system for detecting glucose in the medical fluid. The giving set may or may not comprise a medical or surgical line 5, and may or may not comprise a bag of medical fluid 60. The safety warning system 101 may be the safety warning system described above in respect of any of FIG. 2 to 6, or may be a variant thereof.

For example, a giving set for use as an arterial monitoring or flush system may comprise a medical or surgical line 5, a spike for insertion into a bag of medical fluid 60 and configured to irreversibly couple the bag 60 to the medical or surgical line 5, a receptacle 103 for receiving the medical fluid from the line 5 and an indicator 103 arranged to contact the medical fluid and configured to provide an indication of whether the fluid comprises glucose. The receptacle 103 may allow gas to be flushed from the medical or surgical line 5 and retain medical fluid received from the line 5.

The giving set may further comprise at least one of a three-way port 40 and/or a transducer for monitoring a parameter of the fluid in the medical or surgical line 5, a cannula 10 for insertion into a patient, a port 20, and a syringe 30.

Components of the giving set may also be coupled together, for example mechanically coupled, so that components are not lost or misplaced. For example, the safety warning system 101 may be mechanically coupled to the line 5, for example via a lanyard, so that even if the safety warning system 101 is removed from the line 5 it is not lost or misplaced. In this way, if the safety warning system 101 provides an indication that glucose is present, even if the safety warning system 101 is removed from an outlet of the line 5, it remains coupled to the line 5 thereby providing an indication to the user of whether the line 5 contained glucose.

Another example giving set may comprise two receptacles configured to perform different clinical functions. For example, the giving set may comprise a first receptacle 905, such as a syringe for receiving fluid from a medical or surgical line 5, that is configured to prepare the line 5 for use, for example by displacing any gas in the line 5 with medical liquid such as liquid saline by drawing liquid saline from a bag of medical fluid 60 coupled to the line 5. The giving set also comprises a second receptacle 910 such as a syringe for drawing samples of fluid such as blood from the line 5 for testing, although other receptacles may be used. The first receptacle 905 comprises a safety warning system 101 such as the safety warning system 101 described above in relation to FIGS. 1 to 6. The second receptacle may comprise an anticoagulant. The medical or surgical line may be the medical or surgical line 5 described above in relation to FIGS. 1 to 6. Providing, in a single sterile pack, a first receptacle 905, along with the second receptacle 910 that is adapted for drawing samples of fluid from the line 5, means that a user, such as a clinician, has to take an active step of discarding the first receptacle 905 when using the second receptacle 910. A user is therefore reminded to use the specific first receptacle 905 (comprising the safety warning system 101) provided in the pack with the second receptacle 910, thus improving uptake in use of the safety warning system 101.

Figure 7:
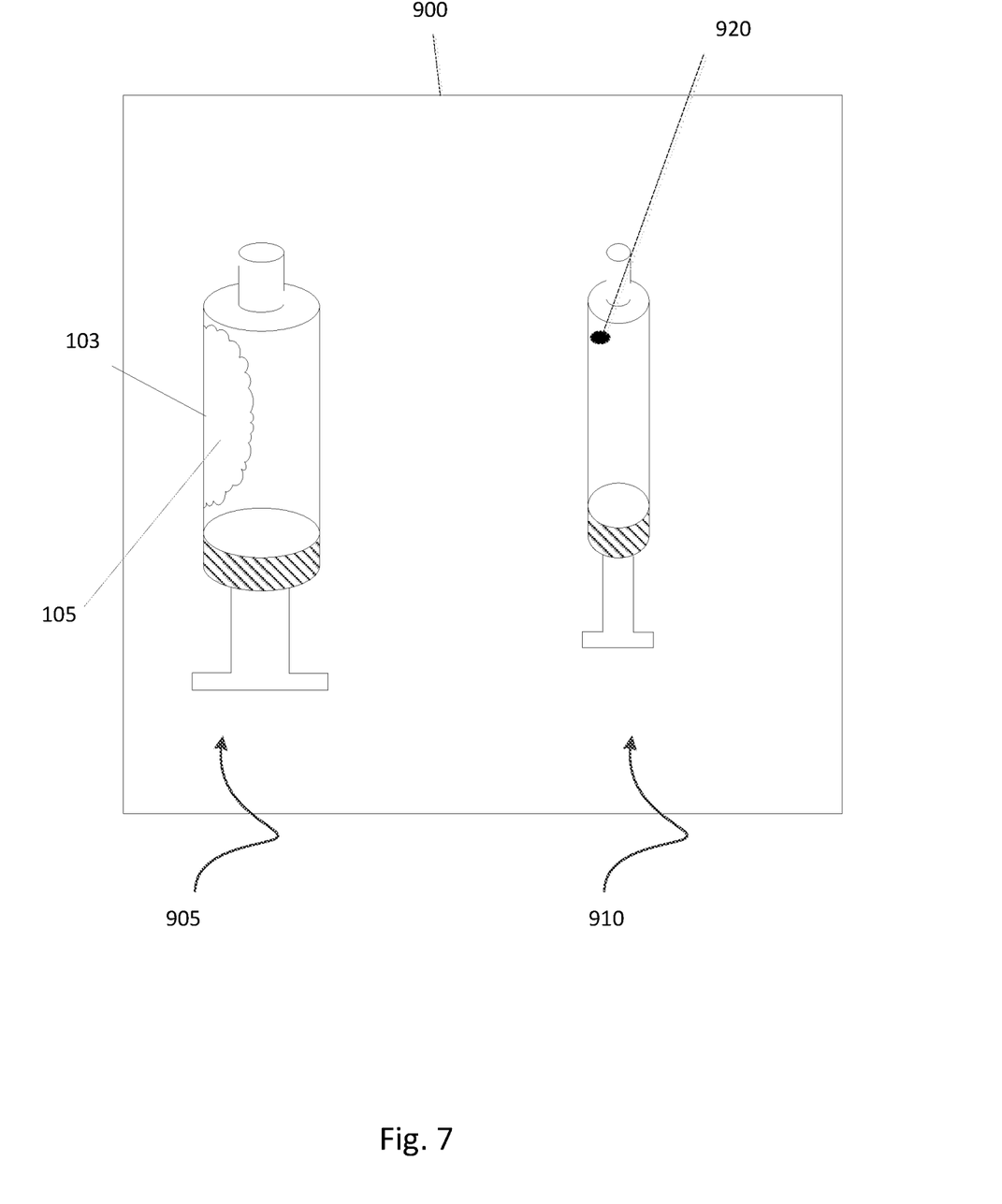
FIG. 7 shows a schematic view of an example giving set comprising an example safety warning system.

An example giving set 900 is shown in FIG. 7. The giving set 900 shown in FIG. 7 is a sealed sterile pack. The sealed sterile pack comprises a first receptacle 905 and a second receptacle 910.

The first receptacle 905 shown in the example of FIG. 7 is a syringe, and is configured to receive fluid from a medical or surgical line. The first receptacle 905 comprises an indicator 105 arranged to contact medical fluid received, for example drawn or displaced, from a medical or surgical line, and is configured to provide an indication of whether the fluid comprises glucose. In the example shown in FIG. 7, the first receptacle 905 comprises a safety warning system 101, for example the safety warning system 101 described above. The first receptacle 905 is adapted to draw fluid from the line 5 such that any gas in the line 5 is removed from the line 5. In this way the cavity of the first receptacle 905 may act as a deadspace. In some examples, the first receptacle 905 may have a larger cavity than the second receptacle 910 to perform this function. For example, the first receptacle 905 may have a cavity with a volume of at least 5 mL, at least 10 mL, at least 30 mL.

The second receptacle 910 shown in the example of FIG. 7 is also a syringe, and is adapted for sampling fluid, such as blood, from a medical or surgical line 5. In the example shown in FIG. 7, the second receptacle 910 is smaller than the first receptacle 905. The second receptacle 910 comprises an anticoagulant 920 such as Heparin for this purpose. The second receptacle 910 may have a cavity with a volume of at least 2 mL and less than 5 mL.

In use, the first receptacle 905 is operated by a user, such as a clinician, to draw an initial quantity of fluid from the medical or surgical line 5. This may be to prepare the line for use. If glucose is present in the fluid, the indicator 105 in the first receptacle 905 provides an indication to the user so that the user knows that the fluid contains glucose. If glucose is not present, the user may then connect the second receptacle 910 to the line 5 for sampling from the line 5. Because the samples drawn from the line 5 may contain blood, the second receptacle 910 comprises an anticoagulant such as Heparin to prevent clotting in the second receptacle 910 so that the sample may be effectively tested.

In some examples the first receptacle 905 and the second receptacle 910 are coupled together, for example mechanically coupled, such as via a lanyard. The first receptacle 905 and the second receptacle 910 may also be coupled together by being held in a common enclosure, such as a net or perhaps the sterile pack of the giving set. Coupling the two receptacles 905, 910 together may help prevent the first receptacle 905, comprising a safety warning system 101, from being accidentally displaced or discarded, and may help to ensure the specific first receptacle 905, comprising the safety warning system 101, is used with the second receptacle 910.

The giving set 900 may also comprise other components such as coupling means, such as a Luer® lock connector, for coupling or connecting the receptacles 905, 910 to a line. The giving set 900 may also comprise the medical or surgical line 5. The first receptacle 905 may be pre-coupled to the line 5 so that a clinician does not forget to couple the first receptacle 905 to the line 5 before use.

In all of the examples described above, the indicator 105 may be configured to provide an indication of whether the fluid comprises glucose when the concentration of glucose in solution is greater than or equal to 10 mMol, greater than or equal to 100 mMol, greater than or equal to 300 mMol.

In all of the examples described above, the indicator 105 may cause writing or words to be displayed such as GLUCOSE or DANGER or DO NOT USE, but many other examples or pictures or symbols are possible, such as a skull and crossbones. In some examples, if glucose is not present the indicator 105 may provide an indication to the user, for example the indicator 105 may provide a reassuring word such as SAFE or SAFE TO USE or the like or pictures or symbols could be displayed.

The indicator 105 may also be configured to remain in the receptacle 103, 905 so as not to contaminate the line 5. For example, the indicator 105 may be highly viscous, for example more viscous than the medical fluid, so that it does not flow out of the receptacle 103. The indicator 105 may also be insoluble in a medical fluid such as a liquid saline solution. The indicator 105 may be porous, for example the indicator 105 may be a gel or integrated in a mesh or web-like structure, into which the medical fluid can soak in. The indicator 105 may be adhered to or integrated in to a surface of the safety warning system 101, such as a wall of the receptacle 103, 905. For example, the indicator 105 may be a coating on a wall or surface of the receptacle 103, 905, the one-way valve 115 or the gas release path 110. In such examples, a one-way valve 115 may not be necessary to prevent contamination of the line 5 because the indicator 105 will not flow into the line 5. The indicator 105 may also be configured to draw fluid from the receptacle 103, 905 and/or line 5, for example via capillary action or diffusion.

Although the indicator 105 described above is a chemical indicator that changes colour in contact with a glucose-containing solution, in other examples the indicator 105 may be an electronic indicator. For example, an electronic indicator may be battery operated.

An indicator such as an electronic indicator may be integral to the safety warning system 101. The electronic indicator may also be integral to line 5 such that the electronic indicator is adapted to contact fluid in the line 5. The electronic indicator may be configured to draw a sample of fluid from the line 5, for example via capillary action. The line 5 may provide a gas release path to enable fluid upstream in the line 5 to displace gas in the line adjacent to the electronic indicator to contact the electronic indicator.

An indicator 105 may also be part of other components of an arterial or venous monitoring system, such as the system described above in relation to FIG. 1. For example, an indicator 105 may be part of a sampling system of an arterial or venous monitoring or flush system.

For example, an indicator 105 may be included as part of sampling connector in an arterial or venous monitoring or flush system, for example a sampling connector for use as an adaptor for a three-way tap arterial blood sampling device, such as that described in EP 282806. The three-way tap arterial blood sampling device may be configured to sample fluid from a line such as line 5 shown in FIG. 1. The sampling connector may comprise at least two apertures in fluid communication via a fluid flow conduit and a one-way valve disposed to allow fluid to flow from the first aperture, through the fluid flow conduit and out of the second aperture, but not to allow fluid to flow into the second aperture and through the fluid flow conduit to the first aperture. The first aperture may be within a male end and the second aperture may be within a female end. The male end of the sampling connector may be a Luer® lock connector with an altered taper or altered dimensions so as to fit firmly or jam when connected to a female sampling port of the sampling device, such that the sampling connector is reversibly connectable to the sampling device and is difficult to disconnect from the sampling device, wherein in use a user is impeded from removing the sampling connector. An indicator 105 may be included as part of the sampling connector, for example, in the fluid flow conduit, or to one side of the one-way valve, for example as part of the second aperture.

An indicator 105 such as an electronic indicator may also be part of the three-way port 40 or the monitor 50 shown in FIG. 1. For example, the electronic indicator may comprise a sensor that is included as part of the three-way port 40 shown in FIG. 1, or as part of the transducer.

In some examples, an electronic indicator may comprise a sensor and a control unit. The sensor may be configured to contact fluid in a medical or surgical line, such as the line 5 described above, and send a signal to the control unit. The sensor may be adapted specifically to monitor glucose, or it may be adapted to monitor other parameters, such as a parameter of a patient such as blood pressure. The control unit may be configured to receive signals from the sensor and process the received signals to make a determination of whether the fluid contains glucose. In response to determining that the fluid contains glucose, the control unit may further be configured to provide an alert in response to the control unit determining the presence of glucose. The alert may comprise an alarm, such as an audible alarm and/or a visual alert. Additionally or alternatively, the control unit may be configured to inhibit or stop the flow of fluid through the line 5 in response the control unit determining the presence of glucose, for example by controlling a tap or valve coupled to the line 5. For example, the alert may comprise a signal configured to inhibit or stop the flow of fluid through the line 5.

The control unit may be included as part of the monitor 50 described above in relation to FIG. 1. For example, the control unit may also be configured to receive signals relating to a parameter of a patient, for example a blood pressure, from the sensor or from a second sensor. The sensor may be the transducer in the three-way port 40 described above in relation to FIG. 1. The control unit may be configured to process these received signals and make a determination of the parameter of the patient in addition to making a determination of whether fluid in the line 5 comprises glucose.

Although visual indications have been described above, the indicator 105 may additionally or alternatively be configured to provide an audible indication, such as an alarm or beep. For example, the monitor 50 may configured to provide an audible alarm.

In some examples the safety warning system 101 may be configured so that the fluid contacts the indicator 105 by at least one of capillary action and diffusion. For example, the safety warning system 101 may be a collar that surrounds the line 5. The collar may comprise the indicator 105, for example the indicator 105 may be integrated into a mesh or web that surrounds the line 5 and is adapted to contact fluid in the line 5. The indicator 105 may be configured to draw fluid, for example liquid, from the line 5 via capillary action or diffusion, and comprises a gas release path 110 that allows any gas in the safety warning system 101 and the line 5 to be displaced by fluid.

In some examples the safety warning system 101 may also be configured to provide a back pressure to the line 5 sufficient for arterial monitoring, once the receptacle 103 has received the fluid from the line 5. For example, the safety warning system is configured to provide a back pressure of at least 100, at least 200, at least 300 mmHg. This may allow the safety warning system 101 to remain coupled to the line 5 in use, for example in an arterial monitoring system such as the one shown in FIG. 1, although of course the safety warning system 101 may be adapted for use with venous systems.

In some examples the receptacle 103 may be arranged to draw fluid from the line into the cavity. For example, the receptacle 103 may comprise a negative pressure region, for example a region with a pressure less than ambient, such as less than 1 atmosphere. For example, the receptacle 103 may have a cavity with a negative pressure region. The receptacle 103 may be evacuated, for example the receptacle 103 may comprise a vacuum. Fluid may be displaced from the line 5 into the receptacle. In such examples, the safety warning system 101 may comprise a valve or tap, for example coupled to the receptacle 103, to open the cavity to the line 5 when the safety warning system 101 is coupled to the line 5, to draw fluid from the line 5. The receptacle 103 may also comprise a one-way valve 115 as described above to inhibit loss of the fluid once it has been received.

The safety monitoring system 101 may also comprise instructions for use by a clinician. For example, the receptacle 103 may comprise instructions printed thereon for use of the safety warning system 101. A giving set may additionally or alternatively comprise instructions for use by a clinician. The instructions may comprise pictorial representations of how to use the receptacle, for example.

Although the bag of medical fluid 60 described in the examples above is a liquid saline solution, it will be understood that in other examples the medical fluid is not limited to liquid saline solutions.

In some examples a vessel such as a bag or syringe is supplied at an outlet of the arterial sampling system to receive fluid during the initial flushing process, the vessel containing some glucose detecting mechanism.

In some examples, the safety monitoring system 101 is a cap or elongated cap or length of tubing or the like which allows flushing of the arterial system through the cap wherein the fluid comes into contact with the colour changing detection medium, causing colour change. The colour change may be in the whole or a portion of the device or may spell out specific words, for example GLUCOSE or DANGER or DO NOT USE, but many other examples or pictures or symbols are possible. In one example, if glucose is not present a reassuring word such as SAFE or SAFE TO USE or the like or pictures or symbols could be displayed.

Aspects of the disclosure require the use of a glucose detector in the monitoring system, pressure transducing and flush tubing which is in contact with the fluid within the system or being removed from the system.

In one example this is an electronic glucose detector with an alarm state indicating that a glucose solution has been used in error and in another example it is a colour changing indicator.

In one example a colour change may spell warning words to alert the user that glucose is present.

In one example the glucose oxidase/colour indicator commonly used on blood or urine glucose test strips is used.

In one example a sampling connector may incorporate the colour change component.

In one example a quantity of glucose colour changing indicator is located in the sampling connector so that when fluid is drawn from the sampling connector it will be coloured if glucose is present thereby indicating to the clinician that an error has occurred.

In one example a vessel such as a bag or syringe is supplied at an outlet of the arterial sampling system to receive fluid during the initial flushing process, the vessel containing some glucose detecting mechanism.

In the context of the present disclosure other examples and variations of the apparatus and methods described herein will be apparent to a person of skill in the art.

The invention claimed is:

1. A safety warning system for detecting glucose in an arterial or venous monitoring or flush system, wherein the monitoring or flush system comprises a medical or surgical line for connecting to a patient, the safety warning system comprising:
   a receptacle into which exogenous fluid is configured to be displaced from the medical or surgical line; and
   a color change indicator disposed within the receptacle and arranged to contact the exogenous fluid from the medical or surgical line, the color change indicator configured to provide a visual indication of whether the exogenous fluid traversing through the medical or surgical line comprises glucose and to alert a user of the safety warning system for detecting glucose in the arterial or venous monitoring or flush system if the exogenous fluid contained within the medical or surgical line comprises glucose;
   wherein:
      the receptacle is expandable and comprises a syringe operable by a user; and expanding the receptacle creates a negative pressure region in the receptacle, connectable to draw exogenous fluid through the medical or surgical line.

2. The safety warning system of claim 1 wherein:
the receptacle further comprises a gas release path to enable the exogenous fluid to displace gas to contact the color change indicator,
the color change indicator is configured to warn of a presence of glucose in the exogenous fluid.

3. The safety warning system of claim 1 further comprising a one-way valve configured to allow fluid to flow from the medical or surgical line into the receptacle.

4. The safety warning system of claim 2 wherein the gas release path comprises a valve which blocks in contact with liquid.

5. The safety warning system of claim 1 wherein the receptacle is configured to expand to receive a volume of fluid greater than or equal to an internal volume of the medical or surgical line.

6. The safety warning system of claim 1 further comprising a one-way valve wherein:
the medical or surgical line has a first end and a second end,
the first end is coupled to the patient,
the second end is coupled to a bag of the exogenous fluid, and
the one-way valve is configured to allow the exogenous fluid to flow from the bag through the medical or surgical line into the receptacle.

7. The safety warning system of claim 1 wherein the safety warning system is configured to receive the exogenous fluid from the medical or surgical line into the receptacle by bulk flow.

8. The safety warning system of claim 1 configured so that the exogenous fluid contacts the color change indicator by at least one of capillary action and diffusion.

9. The safety warning system of claim 1 wherein the safety warning system is configured to provide a back pressure to the medical or surgical line sufficient for arterial monitoring once the receptacle has received the exogenous fluid from the medical or surgical line.

10. The safety warning system of claim 1 wherein the color change indicator is arranged to contact fluid in the receptacle.

11. The safety warning system of claim 10 wherein the color change indicator comprises an indicator selected from a group of indicators consisting of: (i) a chemical indicator configured to remain within the receptacle to not contaminate the medical or surgical line, and (ii) an electronic sensor for sensing a presence of glucose in a solution in the receptacle.

12. The safety warning system of claim 1 wherein the color change indicator comprises a color changing fluid that changes color in a presence of a solution comprising glucose.

13. The safety warning system of claim 1 wherein the color change indicator is configured to display symbols and/or writing in a presence of a solution containing glucose.

14. The safety warning system of claim 1 adapted for use with an invasive (intra-arterial) blood pressure monitoring system.

15. The safety warning system of claim 1 wherein the arterial monitoring or flush system is adapted to receive fluid from an arterial or venous line.

16. The safety warning system of claim 9 wherein the back pressure to the medical or surgical line sufficient for the arterial monitoring comprises a pressure of at least 100 mmHg.

17. The safety warning system of claim 12 wherein the color changing fluid comprises at least one of glucose oxidase and peroxidase.

18. The safety warning system of claim 15 wherein the receptacle is adapted to receive fluid from an outlet of the arterial monitoring or flush system.

* * * * *